US012766078B2

(12) United States Patent
Kaminosono et al.

(10) Patent No.: US 12,766,078 B2
(45) Date of Patent: Oct. 20, 2026

(54) FIT CHECKING MATERIAL COMPOSITION FOR DENTAL USE

(71) Applicant: GC Corporation, Shizuoka (JP)

(72) Inventors: Yoshiya Kaminosono, Tokyo (JP); Jun Sato, Tokyo (JP)

(73) Assignee: GC Corporation, Shizuoka (JP)

(*) Notice: Subject to any disclaimer, the term of this patent is extended or adjusted under 35 U.S.C. 154(b) by 195 days.

(21) Appl. No.: 18/730,159

(22) PCT Filed: Nov. 15, 2022

(86) PCT No.: PCT/JP2022/042442
§ 371 (c)(1),
(2) Date: Jul. 18, 2024

(87) PCT Pub. No.: WO2023/139905
PCT Pub. Date: Jul. 27, 2023

(65) Prior Publication Data

US 2025/0143977 A1 May 8, 2025

(30) Foreign Application Priority Data

Jan. 20, 2022 (JP) ................................ 2022-007298

(51) Int. Cl.
*A61K 6/25* (2020.01)

(52) U.S. Cl.
CPC .................................... *A61K 6/25* (2020.01)

(58) Field of Classification Search
None
See application file for complete search history.

(56) References Cited

U.S. PATENT DOCUMENTS

| | | | | |
|---|---|---|---|---|
| 4,273,902 | A * | 6/1981 | Tomioka et al. | C08K 3/08 525/478 |
| 4,891,400 | A * | 1/1990 | Schwabe et al. | C08K 5/01 524/745 |
| 5,661,222 | A | 8/1997 | Hare | |
| 6,495,614 | B1 * | 12/2002 | Kamohara et al. | 523/116 |
| 2009/0247663 | A1 | 10/2009 | Kamohara et al. | |

FOREIGN PATENT DOCUMENTS

| | | |
|---|---|---|
| JP | H02-262502 | 10/1990 |
| JP | H05-154168 | 6/1993 |
| JP | H07-088123 | 4/1995 |
| JP | H11-335224 | 12/1999 |
| JP | 2009-242322 | 10/2009 |
| TW | 289041 | 10/1996 |

OTHER PUBLICATIONS

International Search Report mailed on Jan. 31, 2023 with respect to PCT/JP2022/042442.

* cited by examiner

*Primary Examiner* — Robert A Wax
(74) *Attorney, Agent, or Firm* — IPUSA, PLLC

(57) ABSTRACT

A fit checking material composition for dental use includes a first paste and a second paste. A mixture of the first paste and the second paste 35 seconds after mixing the first paste and the second paste, has a consistency of 37 mm or greater and 43 mm or less at 23° C.

3 Claims, No Drawings

FIT CHECKING MATERIAL COMPOSITION FOR DENTAL USE

TECHNICAL FIELD

The present invention relates to a fit checking material composition for dental use.

BACKGROUND ART

In dental treatments, fit checking materials are widely used. A fit checking material is applied to an inner surface of a dental prosthesis, and the fit checking material is cured in a state where the prosthesis is set in an oral cavity. Then, the prosthesis is taken out from the oral cavity, and the fit of the dental prosthesis is determined based on the fit checking material cured on the inner surface of the prosthesis.

In a case where there is an undesirable contact between the inner surface of the dental prosthesis and a supporting tooth or oral mucosa, part of the inner surface of the dental prosthesis is strongly brought into contact with the supporting tooth or oral mucosa so that a film of the fit checking material formed on the strongly contacted site of the inner surface of the dental prosthesis becomes thinner than other parts of the film of the fit checking material. By polishing an area of the dental prosthesis where the film of the fit checking material becomes thin, a partial unsuitable fit of the dental prosthesis can be corrected.

Patent Document 1 discloses a paste for examining a denture base overpressure part, where the paste includes polydiorganosiloxane, a pigment, and a water-soluble polymer powder.

CITATION LIST

Patent Document

Patent Document 1: Japanese Patent No. 2650060

SUMMARY OF INVENTION

Technical Problem

However, fit checking materials for dental use of related art have a problem associated with easiness of checking a fit.

An object of the present invention is to provide a fit checking material for dental use, which facilitates fitting checks.

Solution to Problem

According to one aspect of the present invention, a fit checking material composition for dental use includes a first paste and a second paste. A mixture of the first paste and the second paste 35 seconds after mixing the first paste and the second paste has a consistency of 37 mm or greater and 43 mm or less at 23° C.

Advantageous Effects of Invention

According to one aspect of the present invention, a fit checking material, which facilitates fitting checks, can be provided.

DESCRIPTION OF EMBODIMENTS

In the following, embodiments of the present invention will be described.

The fit checking material composition for dental use of the present embodiment includes a first paste and a second paste. In the present specification, the fit checking material for dental use encompasses a material for measuring a fit between an inner surface of a dental prosthesis and a supporting tooth or oral mucosa.

The first paste can function as a catalyst paste in the fit checking material composition for dental use. Moreover, the second paste can function as a base paste in the fit checking material composition for dental use. The fit checking material composition for dental use of the present embodiment is obtained as a mixture prepared by mixing the first paste and the second paste.

Blending amounts of the first paste and second paste are arbitrary. For example, a mass ratio between the first paste and the second paste in the fit checking material composition for dental use is from 8:2 to 2:8, preferably from 7:3 to 3:7, and more preferably from 6:4 to 4:6.

According to the fit checking material composition for dental use of the present embodiment, a consistency of a mixture obtained by mixing the first paste and the second paste is 37 mm or greater and 43 mm or less, preferably 38 mm or greater and 42 mm or less, and more preferably 38 mm or greater and 41 mm or less. The consistency is a consistency of the mixture of the first paste and the second paste 35 seconds after mixing the first paste and the second paste at 23° C.

According to the fit checking material composition for dental use of the present embodiment, as described above, the consistency of the mixture of the first paste and the second paste is 37 mm or greater and 43 mm or less, thus the mixture can be inhibited from freely flowing on an inner surface of a dental prosthesis. Thus, the fit checking material composition for dental use of the present embodiment can facilitate fitting checks because the mixture is uniformly spread between an inner surface of a dental prosthesis and a supporting tooth or oral mucosa.

Moreover, according to the fit checking material composition for dental use of the present embodiment, the consistency of the mixture of the first paste and the second paste is 37 mm or greater and 43 mm or less so that difficulty in extrusion of the mixture from a dispenser or the like, or poor mixing of the pastes can be avoided. Therefore, the fit checking material composition for dental use of the present embodiment can be effortlessly handled.

Moreover, a viscosity of the first paste and a viscosity of the second paste before mixing are both preferably 20,000 mPa·s or greater and 60,000 mPa·s or less, more preferably 21,000 mPa·s or greater and 55,000 mPa·s or less, and yet more preferably 22,000 mPa·s or greater and 50,000 mPa·s or less. In the present specification, the viscosity is a viscosity at 23° C. with a shear rate of 100 (l/s).

According to the fit checking material composition for dental use of the present embodiment, as described above, the viscosity of the first paste and the viscosity of the second paste before mixing are 20,000 mPa·s or greater and 60,000 mPa·s or less so that the mixture is inhibited from freely flowing on an inner surface of a dental prosthesis. Therefore, the fit checking material composition for dental use of the present embodiment facilitates fitting checks of an inner surface of a dental prosthesis because the mixture is uniformly spreadable between the inner surface of the dental prosthesis and a supporting tooth or oral mucosa.

Moreover, according to the fit checking material composition for dental use of the present embodiment, as described above, the viscosity of the first paste and the viscosity of the second paste before mixing are 20,000 mPa·s or greater and 60,000 mPa·s or less so that the mixture is unlikely to be broken off when the mixture cured on an inner surface of a dental prosthesis is peeled off. Therefore, the fit checking material composition for dental use of the present embodiment enables effortless removal of the mixture from an inner surface of a dental prosthesis after checking a fit of the inner surface of the dental prosthesis.

A composition of the fit checking material composition for dental use according to the present embodiment is not particularly limited. For example, the composition includes a composition that is an addition-type silicone composition, and is different from a condensation-type silicone composition.

The addition-type silicone composition is not particularly limited. For example, the addition-type silicone composition includes organopolysiloxane, organohydrogenpolysiloxane, a silicone-soluble platinum compound, and an inorganic filler.

[Organopolysiloxane]

The organopolysiloxane is not particularly limited. The organopolysiloxane is preferably organopolysiloxane including at least two unsaturated aliphatic hydrocarbons per molecule, and is more preferably organopolysiloxane including alkenyl groups.

The organopolysiloxane including alkenyl groups is preferably represented by an average composition formula of $$R^1_aSiO_{(4-a)/2}$$

(in the formula, $R^1$ is a substituted or unsubstituted monovalent hydrocarbon group having a carbon number of 1 to 10, preferably 1 to 8, a is from 1.95 to 2.05, preferably from 2.00 to 2.02, where among the number of $R^1$ groups represented by a, from 0.0001 mol % to 20 mol %, more preferably from 0.001 mol % to 10 mol %, and yet more preferably 0.01 mol % to 5 mol % is an alkenyl group having a carbon number of 2 to 8, preferably 2 to 6).

Examples of the monovalent hydrocarbon group represented by $R^1$ include: alkyl groups, such as methyl groups, ethyl groups, propyl groups, isopropyl groups, butyl groups, isobutyl groups, tert-butyl groups, pentyl groups, neopentyl groups, hexyl groups, cyclohexyl groups, octyl groups, nonyl groups, and decyl groups; aryl groups, such as phenyl groups, tolyl groups, xylyl groups, and naphthyl groups; aralkyl groups, such as benzyl groups, phenylethyl groups, and phenylpropyl groups; alkenyl groups, such as vinyl groups, allyl groups, propenyl groups, isopropenyl groups, butenyl groups, hexenyl groups, cyclohexenyl groups, and octenyl groups; and the like.

Examples of a substituent of $R^1$ include: halogen atoms, such as fluorine atoms, bromine atoms, and chlorine atoms; cyano groups; and the like.

Examples of the alkyl group substituted by the substituent include chloromethyl groups, chloropropyl groups, bromoethyl groups, trifluoropropyl groups, cyanoethyl groups, and the like.

Note that, the alkenyl group may be bonded to a silicon atom positioned at a terminal end, or may be bonded to a silicon atom in a site other than the terminal ends. The alkenyl groups are preferably respectively bonded to the both terminal silicon atoms.

$R^1$ that is other than an alkenyl group is preferably a methyl group or a phenyl group.

The organopolysiloxane including alkenyl groups includes an M unit ($R_3SiO_{1/2}$) and a D unit ($R_2SiO$), and may further include a T unit ($RSiO_{3/2}$).

Moreover, the organopolysiloxane including alkenyl groups may be a homopolymer or a copolymer.

Examples of the organopolysiloxane including alkenyl groups include vinyldimethylsiloxy-terminated dimethylpolysiloxane in which both terminal ends are blocked with a vinyldimethylsiloxy group, methyldivinylsiloxy-terminated dimethylpolysiloxane in which both terminal ends are blocked with a methyldivinylsiloxy group, a vinyldimethylsiloxy-terminated dimethylsiloxane (80 mol %)-methylphenylsiloxane (20 mol %) copolymer in which both terminal ends are blocked with a vinyldimethylsiloxy group, a vinyldimethylsiloxy-terminated dimethylsiloxane (80 mol %)-diphenylsiloxane (20 mol %) copolymer in which both terminal ends are blocked with a vinyldimethylsiloxy group, a vinyldimethylsiloxy-terminated dimethylsiloxane (90 mol %)-diphenylsiloxane (10 mol %) copolymer in which both terminal ends are blocked with a vinyldimethylsiloxy group, a trimethylsiloxy-terminated dimethylsiloxane-vinylmethylsiloxane copolymer in which both terminal ends are blocked with a trimethylsiloxy group, and the like.

Note that, as the organopolysiloxane including alkenyl groups, two or more thereof may be used in combination.

Among the above-listed examples, the organopolysiloxane including alkenyl groups is preferably vinyldimethylsiloxy-terminated dimethylpolysiloxane in which both terminal ends are blocked with a vinyldimethylsiloxy group.

Note that, a viscosity of the organopolysiloxane (a viscosity at 23° C. with a shear rate of 100 (l/s)) is preferably 7,500 mPa·s or greater and 16,000 mPa·s or less, more preferably 8,000 mPa·s or greater and 15,500 mPa·s or less, and yet more preferably 8,500 mPa·s or greater and 15,000 mPa·s or less.

When the viscosity of the organopolysiloxane is 7,500 mPa·s or greater and 16,000 mPa·s or less, a viscosity of the first paste and a viscosity of the second paste before mixing can be both adjusted to 20,000 mPa·s or greater and 60,000 mPa·s or less. Therefore, a fit checking material composition for dental use, which facilitates fitting checks of an inner surface of a dental prosthesis, and enables effortless removal of the mixture from the inner surface of the dental prosthesis after checking the fit of the inner surface of the dental prosthesis, can be provided.

An amount of the organopolysiloxane in the fit checking material composition for dental use is arbitrary. For example, the amount of the organopolysiloxane is 45% by mass or greater and 80% by mass or less, preferably 50% by mass or greater and 75% by mass or less, and yet more preferably 55% by mass or greater and 708 by mass or less.

The organopolysiloxane is preferably included in both the first paste and the second paste. In this case, the organopolysiloxane includes a first component and a second component, where the first component is included in the first paste and the second component is included in the second paste. An amount of the first component in the first paste is preferably 30% by mass or greater and 50% by mass or less, more preferably 35% by mass or greater and 48% by mass or less, and yet more preferably 40% by mass or greater and 45% by mass or less.

Moreover, an amount of the second component of the organopolysiloxane in the second paste is preferably 50% by mass or greater and 95% by mass or less, more preferably 60% by mass or greater and 93% by mass or less, and yet more preferably 70% by mass or greater and 90% by mass or less.

Moreover, in the fit checking material composition for dental use including the first paste and the second paste, a mass ratio of the second component of the organopolysiloxane to the first component of the organopolysiloxane is preferably 1.1 or greater, more preferably 1.3 or greater, and yet more preferably 1.4 or greater.

Note that, an upper limit of the mass ratio of the second component to the first component is not particularly limited. In view of a suitable curing degree of a mixture of the first paste and the second paste for functioning as the fit checking material for dental use, the mass ratio of the second component to the first component may be 2.1 or less.

[Organohydrogenpolysiloxane]

The organohydrogenpolysiloxane causes hydrosilylation with the organopolysiloxane including unsaturated aliphatic hydrocarbons, thereby curing the fit checking material composition for dental use.

The organohydrogenpolysiloxane is preferably represented by an average composition formula of $$R^2_bH_cSiO_{(4-b-c)/2}$$

(in the formula, $R^2$ is a substituted or unsubstituted monovalent hydrocarbon group having a carbon number of 1 to 10, b is from 0.7 to 2.1, c is from 0.001 to 1.0, and b+c is from 0.8 to 3.0).

The number of hydrosilyl groups in the organohydrogenpolysiloxane is preferably from 2 to 300, more preferably from 3 to 200, and yet more preferably from 4 to 100.

$R^2$ is identical to $R^1$ in the organopolysiloxane including alkenyl groups, but $R^2$ is preferably free from an unsaturated aliphatic bond.

Examples of the organohydrogenpolysiloxane include 1,1,3,3-tetramethyldisiloxane, 1,3,5,7-tetramethylcyclotetrasiloxane, methylhydrogencyclopolysiloxane, a methylhydrogensiloxane-dimethylsiloxane cyclic copolymer, tris(dimethylhydrogensiloxy)methylsilane, tris(dimethylhydrogensiloxy)phenylsilane, trimethylsiloxy-terminated methylhydrogenpolysiloxane in which both terminal ends are blocked with a trimethylsiloxy group, a trimethylsiloxy-terminated dimethylsiloxane-methylhydrogensiloxane copolymer in which both terminal ends are blocked with a trimethylsiloxy group, dimethylhydrogensiloxy-terminated dimethylpolysiloxane in which both terminal ends are blocked with a dimethylhydrogensiloxy group, a dimethylhydrogensiloxy-terminated dimethylsiloxane-methylhydrogensiloxane copolymer in which both terminal ends are blocked with a dimethylhydrogensiloxy group, dimethylhydrogensiloxy-terminated methylhydrogenpolysiloxane in which both terminal ends are blocked with a dimethylhydrogensiloxy group, a trimethylsiloxy-terminated methylhydrogensiloxane-diphenylsiloxane copolymer in which both terminal ends are blocked with a trimethylsiloxy group, a trimethylsiloxy-terminated methylhydrogensiloxane-diphenylsiloxane-dimethylsiloxane copolymer in which both terminal ends are blocked with a trimethylsiloxy group, a copolymer including a $(CH_3)_2HSiO_{1/2}$ unit and an $SiO_{4/2}$ unit, a copolymer including a $(CH_3)_2HSiO_{1/2}$ unit, an $SiO_{4/2}$ unit, and a $(C(H_5)SiO_{3/2}$ unit.

The organohydrogenpolysiloxane may be of a straight chain, of a cyclic structure, or of a branched chain.

The number of silicon atoms in the organohydrogenpolysiloxane is preferably from 2 to 1,000, more preferably from 3 to 300, and yet more preferably from 4 to 100.

Note that, as the organohydrogenpolysiloxane, two or more thereof may be used in combination.

Among the above-listed examples, the organohydrogenpolysiloxane is preferably organohydrogenpolysiloxane including at least three hydrogen atoms each directly bonded to a silicon atom per molecule, and more preferably a trimethylsiloxy-terminated dimethylsiloxane-methylhydrogensiloxane copolymer in which both terminal ends are blocked with a trimethylsiloxy group.

Note that, an amount of a hydrogen atom bonded to a silicon atom in the organohydrogenpolysiloxane is preferably 20% by mass or greater and 80% by mass or less, more preferably 25% by mass or greater and 70% by mass or less, and yet more preferably 30% by mass or greater and 60% by mass or less.

A viscosity (viscosity at 23° C. with a shear rate of 100 (l/s)) of the organohydrogenpolysiloxane is preferably 5 mPa·s or greater and 500 mPa·s or less, more preferably 5 mPa·s or greater and 300 mPa·s or less, and yet more preferably 5 mPa·s or greater and 200 mPa·s or less.

An amount of the organohydrogenpolysiloxane in the fit checking material composition for dental use is arbitrary. For example, the amount of the organohydrogenpolysiloxane is 0.1% by mass or greater and 10% by mass or less, preferably 1% by mass or greater and 8% by mass or less, and more preferably 2% by mass or greater and 5% by mass or less.

The organohydrogenpolysiloxane is preferably included in the second paste. In this case, an amount of the organohydrogenpolysiloxane in the second paste is preferably 1% by mass or greater and 20% by mass or less, more preferably 2% by mass or greater and 15% by mass or less, and yet more preferably 3% by mass or greater and 10% by mass or less.

Note that, in the case where the organopolysiloxane is organopolysiloxane including alkenyl groups, a molar ratio of a hydrosilyl group of the organohydrogenpolysiloxane to the alkenyl group of the organopolysiloxane including alkenyl groups is preferably from 0.1 to 4.0.

[Silicone-Soluble Platinum Compound]

As the silicone-soluble platinum compound, a hydrosilylation catalyst can be used.

Examples of the hydrosilylation catalyst include: platinum-based catalysts, such as platinum black, platinum (IV) chloride, chloroplatinic acid, reaction products between chloroplatinic acid and monohydric alcohol, complexes between chloroplatinic acid and olefins, and platinum bisacetoacetate; platinum group metal catalysts, such as palladium-based catalysts, and rhodium-based catalysts; and the like.

Note that, as the hydrosilylation catalyst, two or more thereof may be used in combination.

An amount of the silicone-soluble platinum compound in the fit checking material composition for dental use is arbitrary. For example, the amount of the silicone-soluble platinum compound is 0.01% by mass or greater and 10% by mass or less, preferably 0.1% by mass or greater and 8% by mass or less, and more preferably 0.1% by mass or greater and 5% by mass or less.

The silicone-soluble platinum compound is preferably included in the first paste. In this case, an amount of the silicone-soluble platinum compound in the first paste is preferably 0.05% by mass or greater and 10% by mass or less, more preferably 0.1% by mass or greater and 8% by mass or less, and yet more preferably 0.1% by mass or greater and 5% by mass or less.

[Inorganic Filler]

The inorganic filler is not particularly limited. Examples of the inorganic filler include fumed silica particles, wet silica particles, crystalline silica particles, carbon black, red iron oxide particles, cerium oxide particles, titanium oxide particles, calcium carbonate particles, aluminum hydroxide particles, titanate particles, and the like.

Note that, as the inorganic filler, two or more thereof may be used in combination.

An amount of the inorganic filler in the fit checking material composition for dental use is arbitrary. For example, the amount of the inorganic filler is 10% by mass or greater and 70% by mass or less, preferably 15% by mass or greater and 60% by mass or less, and more preferably 20% by mass or greater and 50% by mass or less.

The inorganic filler is preferably included in both the first paste and the second paste. In this case, an amount of the inorganic filler in the first paste is preferably 1% by mass or greater and 70% by mass or less, more preferably 3% by mass or greater and 70% by mass or less, and yet more preferably 5% by mass or greater and 70% by mass or less. Moreover, an amount of the inorganic filler in the second paste is preferably 1% by mass or greater and 70% by mass or less, more preferably 3% by mass or greater and 60% by mass or less, and yet more preferably 5% by mass or greater and 50% by mass or less.

The fit checking material composition for dental use according to the present embodiment may include various silicone resins, silicone oil, nonionic surfactants, pigments, and the like, as long as properties of the fit checking material composition for dental use are not adversely affected.

[Silicone Oil]

The silicone oil is not particularly limited. Examples of the silicone oil include methylphenylpolysiloxane, dimethylpolysiloxane, and the like.

An amount of the silicone oil in the fit checking material composition for dental use is arbitrary. For example, the amount of the silicone oil is 0.1% by mass or greater and 20% by mass or less, preferably 0.3% by mass or greater and 15% by mass or less, and more preferably 0.5% by mass or greater and 10% by mass or less.

The silicone oil is preferably included in the first paste. In this case, an amount of the silicone oil in the first paste is preferably 0.1% by mass or greater and 25% by mass or less, more preferably 0.5% by mass or greater and 20% by mass or less, and yet more preferably 1% by mass or greater and 15% by mass or less.

[Nonionic Surfactant]

The nonionic surfactant may be optionally added. In view of improvement in hydrophilicity of a mixture of the first paste and the second paste, and uniform spreading of the mixture between an inner surface of a dental prosthesis and a supporting tooth or oral mucosa, a nonionic surfactant is preferably added.

The nonionic surfactant is not particularly limited. Examples of the nonionic surfactant include silicone-based surfactants, hydrocarbon-based surfactants (e.g., polyoxyethylene alkyl ether), fluorocarbon-based surfactants, polyethylene glycol-polypropylene glycol block copolymers, and the like. Among the above-listed examples, the nonionic surfactant is preferably a silicone-based surfactant or a hydrocarbon-based surfactant.

Examples of commercial products of the silicone-based surfactant include KF-351A, KF945, KF640, KF642, KF643, and KF644 (all manufactured by Shin-Etsu Chemical Co., Ltd.), and the like.

Examples of commercial products of the hydrocarbon-based surfactant include NAROACTY (registered trademark) CL40, CL50, CL70, and CL90, SANNONIC (registered trademark) SS30, SS50, SS70, and SS90 (all manufactured by Sanyo Chemical Industries, Ltd.), and the like.

Note that, as the nonionic surfactant, two or more thereof may be used in combination.

An amount of the nonionic surfactant in the fit checking material composition for dental use is arbitrary. For example, the amount of the nonionic surfactant is 0.01% by mass or greater and 3% by mass or less, preferably 0.1% by mass or greater and 2% by mass or less, and more preferably 0.1% by mass or greater and 1% by mass or less.

The nonionic surfactant is preferably included in the second paste. In this case, an amount of the nonionic surfactant in the second paste is preferably 0.1% by mass or greater and 5% by mass or less, more preferably 0.1% by mass or greater and 3% by mass or less, yet more preferably 0.5% by mass or greater and 2% by mass or less.

[Pigment]

The pigment is not particularly limited, but a white pigment is preferably used as the pigment. Examples of the white pigment include titanium oxide, aluminum oxide, zirconium oxide, a mixture of titanium oxide and vinyl polysiloxane, a mixture of titanium oxide, aluminum oxide, and vinyl polysiloxane, a mixture of zirconium oxide and vinyl polysiloxane, and the like. These white pigments in paste form are added to the fit checking material composition for dental use.

Note that, as the pigment, two or more thereof may be used in combination.

An amount of the pigment in the fit checking material composition for dental use is arbitrary. For example, the amount of the pigment is 0.01% by mass or greater and 3% by mass or less, preferably 0.1% by mass or greater and 2% by mass or less, and more preferably 0.5% by mass or greater and 1.5% by mass or less.

The pigment is preferably included in the first paste. In this case, an amount of the pigment in the first paste is preferably 0.1% by mass or greater and 10% by mass or less, more preferably 0.5% by mass or greater and 5% by mass or less, and yet more preferably 1% by mass or greater and 3% by mass or less.

Use of the pigment facilitates a visual check of a difference in thickness over a wide range, and particularly facilitates a visual fitting check of a dental prosthesis formed of ceramics.

As described above, the fit checking material composition for dental use of the present embodiment includes organopolysiloxane including at least two unsaturated aliphatic hydrocarbons per molecule, organohydrogenpolysiloxane including at least three hydrogen atoms each directly bonded to a silicon atom per molecule, a silicone-soluble platinum compound, and an inorganic filler.

According to the fit checking material composition for dental use of the present embodiment, as described above, the consistency of the mixture of the first paste and the second paste 35 seconds after missing the first paste and the second paste at 23° C. can be adjusted to 37 mm or greater and 43 mm or less. Therefore, according to the present embodiment, a fit checking material composition for dental use, which facilitates fitting checks because of uniform spreading of the mixture between an inner surface of a dental prosthesis and a supporting tooth or oral mucosa, and enables effortless handling because of inhibition of difficulty in extrusion of mixture or poor mixing of pastes, can be provided.

Moreover, according to the fit checking material composition for dental use of the present embodiment, the viscosity of the first paste at 23° C. and the viscosity of the second paste at 23° C. can be both adjusted to 20,000 mPa·s or greater and 60,000 mPa·s or less at a shear rate of 100 (l/s). Therefore, according to the fit checking material composition for dental use of the present embodiment, a fit checking material composition for dental use, which facilitates a fitting check of an inner surface of a dental prosthesis, and enables effortless removal of the mixture from the inner surface of the dental prosthesis after checking the fit, can be provided.

Moreover, according to the fit checking material composition for dental use of the present disclosure, as described above, the organopolysiloxane includes a first component and a second component, where the first component is included in the first paste and the second component is included in the second paste, and a mass ratio of the second component to the first component is preferably 1.1 or greater. Therefore, the fit checking material composition for dental use of the present embodiment enables to further facilitate spreading of the mixture between an inner surface of a dental prosthesis and a supporting tooth or oral mucosa, and further facilitates a fitting check of the inner surface of the dental prosthesis.

[Method of Using Fit Checking Material Composition for Dental Use]

The fit checking material composition for dental use of the present embodiment is preferably used as a two-part composition in which the silicone-soluble platinum compound and the organohydrogenpolysiloxane are separated.

According to one example, a mixture in which a first part (first paste) including the silicone-soluble platinum compound and a second part (second paste) including the organohydrogenpolysiloxane are mixed is applied to an inner surface of a dental prosthesis, and then the dental prosthesis is set on a supporting tooth or oral mucosa, followed by leaving to stand at room temperature or heating at 50° C. to 200° C. to cure the applied mixture.

EXAMPLES

Hereinafter, examples of the present invention will be described, but the present invention is not limited to the examples. In the following, numerical values without units are based on mass (parts by mass) unless otherwise specified.

Examples 1 to 6 and Comparative Examples 1 to 5

According to the amounts (parts by mass) of constituent components presented in Tables 1 and 2, a first paste and a second paste were prepared, and the first paste and the second paste were mixed at a ratio of 1:1 to prepare a fit checking material for dental use. The prepared fit checking material for dental use was evaluated. The preparation conditions and evaluation results are presented in Table 1 and Table 2.

Note that, the details of each constituent component in Table 1 and Table 2 are as follows.

Methylphenylpolysiloxane: KF50-100cs (manufactured by Shin-Etsu Silicone)

Crystalline silica: Crystalite (registered trademark) VX-S (manufactured by TATSUMORI LTD.)

Fused silica: Fuselex E2 (manufactured by TATSUMORI LTD.)

Hydrophobic fumed silica: AEROSIL (registered trademark) RX-200 (AEROSIL RX-200 (manufactured by NIPPON AEROSIL CO., LTD.)

Polyoxyethylene alkyl ether: NAROACTY (registered trademark) CL-40 (manufactured by Sanyo Chemical Industries, Ltd.)

<Viscosity Test>

A viscometer (RE-85U, manufactured by Toki Sangyo Co., Ltd.) was used in the test. The measurement was performed while maintaining a constant temperature using 23° C. constant-temperature water. The evaluation was performed using the cone rotor number of 3'×R7.7. The measurement was performed at a shear rate of 100 (1/s).

<Consistency Test>

A consistency was measured according to JIS T 6513-2019 under conditions where a mixing duration was 20 seconds, and timing of applying a load was 35 seconds after the start of mixing. The measuring environment was set at room temperature of 23° C.±1° C. and the humidity of 50%±10%.

<Fit Test>

An impression of an upper jaw was taken to produce a plaster model. On the plaster model, a room temperature polymerizable resin (UNIFAST LAB TYPE B No. 8 live pink, manufactured by GC) was built up to cover the palate part of the plaster model to thereby produce a denture. Thereafter, each of the fit checking materials of Examples and Comparative Examples was deposited on the produced denture, and the denture was pressure-bonded to the palate part of the above-produced plaster model.

In order to simulate wetness of the oral cavity, the plaster model was immersed in water before being pressure-bonded to the denture. Finally, the fit checking material was allowed to cure, followed by taking the denture out from the plaster model to evaluate. A part where the color of the denture was revealed was determined as a contact site.

The evaluation criteria of the fit test was as follows. Note that, A and B were evaluated as being desirable, and C was evaluated as being undesirable.

A: a case where only contact sites were appropriately detected

B: a case where sites other than the contact sites were turned slightly pale.

C: a case where contact sites were not appropriately detected

<Removability Test>

When the cured mixture was removed after obtaining the result of the fit test, removability of the cured mixture was evaluated. The evaluation criteria was as follows. Note that, A and B were evaluated as being desirable, and C was evaluated as being undesirable.

A: a case where the cured mixture could be removed as a lump without any missing part B: a case where the cured mixture could be removed as a lump, but there were missing parts C: a case where the cured mixture could not be removed as a lump, or the cured mixture was broken off at some parts, even if the cured mixture could be removed <Wettability Test>

A contact angle meter (DM-501, manufactured by Kyowa Interface Science Co., Ltd.) was used for the test, and distilled water was used as a measuring solution. At a point when three minutes passed from the completion of mixing, distilled water was dripped on the mixture. In this test, a contact angle of the distilled water that was 30 seconds after the dripping was measured. The lower contact angle was evaluated as the higher wettability (higher hydrophilicity).

<Extrusion Test>

Extrusion from a tube having an opening diameter of 5 mm and extrusion from a cartridge dispenser were evaluated through sensory evaluations. The evaluation criteria was as follows. Note that, A and B were evaluated as being desirable, and C was evaluated as being undesirable.

A: a case where the fit checking material was very easily extruded

B: a case where the fit checking material was easily extruded

C: a case where it was difficult to extrude the fit checking material

TABLE 1

| | Ex. 1 | | Ex. 2 | | Ex. 3 | |
|---|---|---|---|---|---|---|
| Paste | First | Second | First | Second | First | Second |
| Dimethylpolysiloxane in which both terminal ends are blocked with vinyldimethylsiloxy group (viscosity: 14000 mPa · s) | 41 | 86 | 42 | 83 | | 83 |
| Dimethylpolysiloxane in which both terminal ends are blocked with vinyldimethylsiloxy group (viscosity: 9000 mPa · s) | | | | | 41 | |
| Dimethylpolysiloxane in which both terminal ends are blocked with vinyldimethylsiloxy group (viscosity: 7000 mPa · s) | | | | | | |
| Dimethylpolysiloxane in which both terminal ends are blocked with vinyldimethylsiloxy group (viscosity: 3000 mPa · s) | | | | | | |
| Vinyl group-modified silicone resin | | | | | 2 | |
| Dimethylsiloxane-methylhydrogensiloxane copolymer in which both terminal ends are blocked with trimethylsiloxy group (amount of hydrogen atom bonded to silicon atom: 33% by mass, viscosity: 10 mPa · s) | | 5 | | 8 | | 8 |
| Straight-chain methylhydrogenpolysiloxane including 10 mol % of methylhydrogensiloxane unit | | | | | | |
| Methylphenylpolysiloxane (silicone oil having viscosity of 100 mPa · s at 25° C.) | 10 | | 11 | | 10 | |
| Crystalline silica | 41 | | 41 | | 40 | |
| Fused silica | | 1 | | 1 | | 1 |
| Hydrophobic fumed silica | 3 | 7 | 3 | 7 | 4 | 7 |
| Polyoxyethylene alkyl ether | | 1 | | 1 | | 1 |
| Silicone-based surfactant | | | | | | |
| Polypropylene glycol diallyl ether | | | | | | |
| Vinylpolysiloxane-mixed platinum complex | 3 | | 1 | | 1 | |
| Quartz powder (palladium bearing rate: 5% by weight, mean particle diameter: 4 μm) | | | | | | |
| Pigment paste (white), mixture of titanium oxide and vinylpolysiloxane | 2 | | 2 | | 2 | |
| Pigment paste (white), mixture of titanium oxide, aluminum oxide, and vinylpolysiloxane | | | | | | |
| Pigment paste (white), mixture of zirconium oxide and vinylpolysiloxane | | | | | | |
| Pigment paste (blue), mixture of phthalocyanine blue and vinylpolysiloxane | | | | | | |
| (Paste total) | 100 | 100 | 100 | 100 | 100 | 100 |
| Paste mixing ratio, first:second (volume ratio) | 1:1 | | 1:1 | | 1:1 | |
| Paste mixing ratio, first:second (mass ratio) | 7:5 | | 7:5 | | 7:5 | |
| Viscosity of first paste (mPa · s) | 41000 | | 37000 | | 32000 | |
| Viscosity of second paste (mPa · s) | 27000 | | 27000 | | 27000 | |
| Consistency of mixture (mm) | 39 | | 40 | | 41 | |
| Fit test | A | | A | | A | |
| Removability test | A | | A | | A | |
| Wettability test (°) | 58 | | 52 | | 62 | |
| Extrusion test | B | | B | | B | |

| | Ex. 4 | | Ex. 5 | | Ex. 6 | |
|---|---|---|---|---|---|---|
| Paste | First | Second | First | Second | First | Second |
| Dimethylpolysiloxane in which both terminal ends are blocked with vinyldimethylsiloxy group (viscosity: 14000 mPa · s) | 44 | 85 | 41 | 87 | 41 | 86 |
| Dimethylpolysiloxane in which both terminal ends are blocked with vinyldimethylsiloxy group (viscosity: 9000 mPa · s) | | | | | | |
| Dimethylpolysiloxane in which both terminal ends are blocked with vinyldimethylsiloxy group (viscosity: 7000 mPa · s) | | | | | | |
| Dimethylpolysiloxane in which both terminal ends are blocked with vinyldimethylsiloxy group (viscosity: 3000 mPa · s) | | | | | | |
| Vinyl group-modified silicone resin | | | | | | |
| Dimethylsiloxane-methylhydrogensiloxane copolymer in which both terminal ends are blocked with trimethylsiloxy group (amount of hydrogen atom bonded to silicon atom: 33% by mass, viscosity: 10 mPa · s) | | 5 | | 5 | | 5 |
| Straight-chain methylhydrogenpolysiloxane including 10 mol % of methylhydrogensiloxane unit | | | | | | |
| Methylphenylpolysiloxane (silicone oil having viscosity of 100 mPa · s at 25° C.) | 2 | | 10 | | 10 | |
| Crystalline silica | 44 | | 41 | | 41 | |
| Fused silica | | | | 1 | | 1 |
| Hydrophobic fumed silica | 5 | 9 | 3 | 7 | 3 | 7 |
| Polyoxyethylene alkyl ether | | | | | | 1 |
| Silicone-based surfactant | | 1 | | | | |
| Polypropylene glycol diallyl ether | | | | | | |
| Vinylpolysiloxane-mixed platinum complex | 3 | | 3 | | 3 | |
| Quartz powder (palladium bearing rate: 5% by weight, mean particle diameter: 4 μm) | | | | | | |

TABLE 1-continued

| | | | | | | |
|---|---|---|---|---|---|---|
| Pigment paste (white), mixture of titanium oxide and vinylpolysiloxane | 2 | | | | | |
| Pigment paste (white), mixture of titanium oxide, aluminum oxide, and vinylpolysiloxane | | | 2 | | | |
| Pigment paste (white), mixture of zirconium oxide and vinylpolysiloxane | | | | | 2 | |
| Pigment paste (blue), mixture of phthalocyanine blue and vinylpolysiloxane | | | | | | |
| (Paste total) | 100 | 100 | 100 | 100 | 100 | 100 |
| Paste mixing ratio, first:second (volume ratio) | 1:1 | | 1:1 | | 1:1 | |
| Paste mixing ratio, first:second (mass ratio) | 7:5 | | 7:5 | | 7:5 | |
| Viscosity of first paste (mPa · s) | 49000 | | 41000 | | 41000 | |
| Viscosity of second paste (mPa · s) | 33000 | | 23000 | | 27000 | |
| Consistency of mixture (mm) | 37 | | 40 | | 39 | |
| Fit test | A | | A | | A | |
| Removability test | A | | A | | A | |
| Wettability test (°) | 45 | | 110 | | 51 | |
| Extrusion test | B | | B | | B | |

TABLE 2

| | Comp. Ex. 1 | | Comp. Ex. 2 | | Comp. Ex. 3 | |
|---|---|---|---|---|---|---|
| Paste | First | Second | First | Second | First | Second |
| Dimethylpolysiloxane in which both terminal ends are blocked with vinyldimethylsiloxy group (viscosity: 14000 mPa · s) | | | | | | |
| Dimethylpolysiloxane in which both terminal ends are blocked with vinyldimethylsiloxy group (viscosity: 9000 mPa · s) | 47 | | | | | |
| Dimethylpolysiloxane in which both terminal ends are blocked with vinyldimethylsiloxy group (viscosity: 7000 mPa · s) | | | 88 | | | |
| Dimethylpolysiloxane in which both terminal ends are blocked with vinyldimethylsiloxy group (viscosity: 3000 mPa · s) | | 83 | | 79 | 42 | 55 |
| Vinyl group-modified silicone resin | | | | | | |
| Dimethylsiloxane-methylhydrogensiloxane copolymer in which both terminal ends are blocked with trimethylsiloxy group (amount of hydrogen atom bonded to silicon atom: 33% by mass, viscosity: 10 mPa · s) | | 8 | | 10 | | 2 |
| Straight-chain methylhydrogenpolysiloxane including 10 mol % of methylhydrogensiloxane unit | | | | | | |
| Methylphenylpolysiloxane (silicone oil having viscosity of 100 mPa · s at 25° C.) | | | | | | |
| Crystalline silica | 47 | | | | 50 | 34 |
| Fused silica | | | | | | |
| Hydrophobic fumed silica | 5 | 8 | 9 | 8 | 7 | 5 |
| Polyoxyethylene alkyl ether | | | | | | |
| Silicone-based surfactant | | 1 | | 1 | | 1 |
| Polypropylene glycol diallyl ether | | | | | | |
| Vinylpolysiloxane-mixed platinum complex | 1 | | 3 | 2 | 1 | |
| Quartz powder (palladium bearing rate: 5% by weight, mean particle diameter: 4 μm) | | | | | | |
| Pigment paste (white), mixture of titanium oxide and vinylpolysiloxane | | | | | | 3 |
| Pigment paste (white), mixture of titanium oxide, aluminum oxide, and vinylpolysiloxane | | | | | | |
| Pigment paste (white), mixture of zirconium oxide and vinylpolysiloxane | | | | | | |
| Pigment paste (blue), mixture of phthalocyanine blue and vinylpolysiloxane | | | | | | |
| (Paste total) | 100 | 100 | 100 | 100 | 100 | 100 |
| Paste mixing ratio, first:second (volume ratio) | 1:1 | | 1:1 | | 1:1 | |
| Paste mixing ratio, first:second (mass ratio) | 7:5 | | 5:5 | | 6:5 | |
| Viscosity of first paste (mPa · s) | 29000 | | 18000 | | 62000 | |
| Viscosity of second paste (mPa · s) | 7000 | | 10000 | | 55000 | |
| Consistency of mixture (mm) | 46 | | 46 | | 34 | |
| Fit test | C | | C | | C | |
| Removability test | B | | C | | C | |
| Wettability test (°) | 107 | | 107 | | 45 | |
| Extrusion test | B | | A | | C | |

| | Comp. Ex. 4 | | Comp. Ex. 5 | |
|---|---|---|---|---|
| Paste | First | Second | First | Second |
| Dimethylpolysiloxane in which both terminal ends are blocked with vinyldimethylsiloxy group (viscosity: 14000 mPa · s) | 41 | 56 | | |
| Dimethylpolysiloxane in which both terminal ends are blocked with vinyldimethylsiloxy group (viscosity: 9000 mPa · s) | | | | |
| Dimethylpolysiloxane in which both terminal ends are blocked with vinyldimethylsiloxy group (viscosity: 7000 mPa · s) | | | | 29 |
| Dimethylpolysiloxane in which both terminal ends are blocked with vinyldimethylsiloxy group (viscosity: 3000 mPa · s) | | | 31 | |
| Vinyl group-modified silicone resin | | | 6 | 6 |
| Dimethylsiloxane-methylhydrogensiloxane copolymer in which both terminal ends are blocked with trimethylsiloxy group (amount of hydrogen atom bonded to silicon atom: 33% by mass, viscosity: 10 mPa · s) | | 3 | | |

TABLE 2-continued

| | | | | |
|---|---|---|---|---|
| Straight-chain methylhydrogenpolysiloxane including 10 mol % of methylhydrogensiloxane unit | | | | 3 |
| Methylphenylpolysiloxane (silicone oil having viscosity of 100 mPa · s at 25° C.) | 10 | 28 | | |
| Crystalline silica | 41 | | 61 | 58 |
| Fused silica | | 1 | | |
| Hydrophobic fumed silica | 3 | 5 | | |
| Polyoxyethylene alkyl ether | | 7 | | |
| Silicone-based surfactant | | | | |
| Polypropylene glycol diallyl ether | | | | 2 |
| Vinylpolysiloxane-mixed platinum complex | 3 | | 1 | |
| Quartz powder (palladium bearing rate: 5% by weight, mean particle diameter: 4 μm) | | | | 2 |
| Pigment paste (white), mixture of titanium oxide and vinylpolysiloxane | 2 | | | |
| Pigment paste (white), mixture of titanium oxide, aluminum oxide, and vinylpolysiloxane | | | | |
| Pigment paste (white), mixture of zirconium oxide and vinylpolysiloxane | | | | |
| Pigment paste (blue), mixture of phthalocyanine blue and vinylpolysiloxane | | | 1 | |
| (Paste total) | 100 | 100 | 100 | 100 |
| Paste mixing ratio, first:second (volume ratio) | 1:1 | | 1:1 | |
| Paste mixing ratio, first:second (mass ratio) | 7:5 | | 5:5 | |
| Viscosity of first paste (mPa · s) | 42000 | | 34000 | |
| Viscosity of second paste (mPa · s) | 30000 | | 13000 | |
| Consistency of mixture (mm) | 35 | | 34.5 | |
| Fit test | C | | C | |
| Removability test | A | | C | |
| Wettability test (°) | 28 | | 110 | |
| Extrusion test | B | | B | |

With reference to Table 1, the compositions, in each of which the consistency of the mixture 35 seconds after mixing the first paste and the second paste at 23° C. was 37 mm or greater 43 mm or less, and the viscosities of the first paste and the second paste at 23° C. with the shear rate of 100 (l/s) were both 20,000 mPa·s or greater and 60,000 mPa·s or less, had the desirable results in all of the fit test, the removability test, and the extrusion test, and had high hydrophilicity (Examples 1 to 6).

With reference to Table 2, conversely, the compositions that did not satisfy the condition where the consistency of the mixture 35 seconds after mixing the first paste and the second paste at 23° C. was 37 mm or greater 43 mm or less, and/or the condition where the viscosities of the first paste and the second paste were both 20,000 mPa·s or greater and 60,000 mPa·s or less had the undesirable result in at least one test among the fit test, the removability test, and the extrusion test (Comparative Examples 1 to 5).

While embodiments of the present invention have been described, the present invention is not limited to specific embodiments, and various modifications and variations are possible within the scope of the invention as claimed.

The present application is based on and claims priority to Japanese Patent Application No. 2022-007298, filed Jan. 20, 2022, the contents of which are incorporated herein by reference in their entirety.

The invention claimed is:

1. A fit checking material composition for dental use, comprising:
- a first paste; and
- a second paste,
- wherein both the first paste and the second paste contain an organopolysiloxane;
- at least one of the first paste and the second paste contains an inorganic filler;
- the second paste contains an organohydrogenpolysiloxane; and
- the first paste contains a silicone-soluble platinum compound,
- wherein
- the organopolysiloxane is a dimethylpolysiloxane in which both terminal ends are blocked with vinyldimethylsiloxy groups and has a viscosity of 7,500 mPa·s or greater and 16,000 mPa·s or less at 23° C. and a shear rate of 100 (1/s);
- the second paste contains the organopolysiloxane in an amount of 70% by mass or greater and 90% by mass or less;
- the organohydrogenpolysiloxane is a dimethylsiloxane-methylhydrogensiloxane copolymer in which both terminal ends are blocked with trimethylsiloxy groups;
- a mixture of the first paste and the second paste 35 seconds after mixing the first paste and the second paste has a consistency of 37 mm or greater and 43 mm or less at 23° C.; and
- the consistency is measured according to JIS T 6513-2019.

2. The fit checking material composition for dental use according to claim 1,
- wherein a viscosity of the first paste at 23° C. and a viscosity of the second paste at 23° C. are both 20,000 mPa·s or greater and 60,000 mPa·s or less at a shear rate of 100 (1/s).

3. The fit checking material composition for dental use according to claim 1,
- wherein the organopolysiloxane includes a first component and a second component, where the first component is included in the first paste and the second component is included in the second paste, and
- wherein a mass ratio of the second component to the first component is 1.1 or greater.

* * * * *